United States Patent [19]

Zeng

[11] Patent Number: 6,021,682
[45] Date of Patent: Feb. 8, 2000

[54] AUTOMATIC MACHINABILITY MEASURING AND MACHINING METHODS AND APPARATUS THEREFOR

[75] Inventor: Jiyue Zeng, Bellevue, Wash.

[73] Assignee: Ingersoll-Rand Company, Woodcliff Lake, N.J.

[21] Appl. No.: 09/143,822

[22] Filed: Aug. 31, 1998

[51] Int. Cl.[7] .................................................. G01N 33/00
[52] U.S. Cl. ............................................................ 73/866
[58] Field of Search ................................ 73/7, 839, 104, 73/866

[56] References Cited

U.S. PATENT DOCUMENTS

| | | | |
|---|---|---|---|
| 3,974,678 | 8/1976 | Rooney et al. | 73/7 |
| 4,941,955 | 7/1990 | Schuster | 204/129.5 |
| 4,966,059 | 10/1990 | Landeck | 83/53 |
| 5,207,533 | 5/1993 | Federspiel et al. | 405/156 |
| 5,501,104 | 3/1996 | Ikeda et al. | 73/629 |

OTHER PUBLICATIONS

Zeng, et al., "Quantitative Evaluation of Machinability in Abrasive Waterjet Machining," Precision Machining: Technology and Machine Development and Improvement; PED–vol. 58, pp. 169–179 (1992).

Jiyue Zeng and Jose P. Munoz, "Intelligent Automation of AWJ Cutting for Efficient Production," *Proceedings of the 12th International Symposium on Jet Cutting Tech.*, pp. 401–408 BHRA, Rouen, France. (1994).

Smariline™ Expert System Software for Fluid Jet Cutting; Ingersoll–Rand® Brochure, 2 pages. (1994).

J. Zeng, J. Munoz, and Ihab Kain, "Milling Ceramics with Abrasive Waterjets—An Experimental Investigation," *Proceedings of the Ninth American Waterjet Conference*: Waterjet Technology Ass'n., Dearborn, MI, pp. 93–108. (Aug. 23–26, 1997).

Zeng, J. and Kim, T., "The Machinability of Porous Material by a High Pressure Abrasive Waterjet," *Proceedings of the Winter Annual Meeting of ASME*, San Francisco, U.S.A., pp. 37–42 (1989).

Ohlsson, et al., "Optimisation of the Piercing or Drilling Mechanism of Abrasive Water Jets," *Proceedings of the 11th Int'l Conference on Jet Cutting Technology*, Scotland, pp. 359–370 (Sep. 1992).

O'Keefe Controls Co. "Air Proximity Sensor" Brochure, Form OK 098 4 pages (1993).

O'Keefe Controls Co. "Products Manufactured" Brochure, Form OK–096 R1 2 pages (1994).

O'Keefe Controls Co. "Accessories for Pneumatic Controls", Brochure, Form OK–063R3, 2 pages (1996).

O'Keefe Controls Co. Air Proximity Sensor System Electric Output Brochure, Form OK–164, 2 pages (not dated).

O'Keefe Controls Co. "Air Proximity Sensor System Pneumatic Output" Brochure, Form OK–165, 2 pages (not dated).

(List continued on next page.)

*Primary Examiner*—Robert Raevis
*Attorney, Agent, or Firm*—Leon Nigohosian, Jr.

[57] ABSTRACT

A method for measuring the machinability of a material which includes piercing a hole through a material to be tested while simultaneously measuring a pierce time duration, T, of the piercing step, and calculating a machinability number from the pierce time duration. Also provided are methods for determining the machining speed of a material and for machining a material which calculate a machining speed for a material based upon the machinability number of the material. The methods used to measure the machinability number and calculate a machining speed for a particular material can include any combination of machining operations, including but not limited to AWJ milling processes. Also provided is an apparatus which detects the time duration a piercing force takes to create a pierce-through condition through a material. The apparatus includes any of a pressure sensor, an acoustic sensor, an optical sensor, a load cell, a mechanical switch, and combinations thereof to measure the pierce-time duration.

22 Claims, 6 Drawing Sheets

OTHER PUBLICATIONS

Quest 2800 Impulse Integrating Sound Level Meter, Quest Technologies Brochure, p. 35 (not dated).

Motion Control Systems, Inc. Acroloop ACR2000 (1–4 Axes Controller), Newsletter, 6 pgs. (Jun. 1997).

"Load Cells" Sens–All, Inc. Advertisement, 1 pg. (not dated).

"Abrasive Water Jets for Demilitarization of Explosive Materials" D. Miller, 8th American Water Jet Conference, p. 457 (not dated).

"Selecting and Justifying a Laser Cutting System: Examining the Benefits of Lasers", Sheet Metal Cutting, pp. 20–23 (not dated).

"New Developments in Laser Fusion Cutting," Sheet Metal Cutting, pp. 68–69 (not dated).

"Cutting with Precision Plasma Technology: Stabilized Jet Helps Improve Cut Quality", Sheet Metal Cutting, pp. 72–73 (not dated).

AUTOMATIC MACHINABILITY MEASURING AND MACHINING METHODS AND APPARATUS THEREFOR

BACKGROUND OF THE INVENTION

This invention relates generally to machining methods and apparatus and more particularly to methods and apparatus for abrasive waterjet machining of engineering materials.

The machinability number is a property of a specific material which varies depending on the type of machining operation, such as milling, to be performed and is related to a number of materials properties. For abrasive waterjet machining of ductile materials, the machinability number is related primarily to flow stress of the material. For abrasive waterjet machining of brittle materials, the machinability is related to the fracture energy, grain size (or flow distribution for materials such as glass), modulus of elasticity and Poisson's ratio.

In a jobshop environment in which a variety of workpiece materials are milled using an abrasive waterjet machining process, if a new type of material is to be milled for the first time, a number of empirical milling tests and calculations must typically be performed to determine the machinability number of the material prior to performing the machining operation.

J. Zeng et al. in the paper titled "The Machinability of Porous Materials by a High Pressure Abrasive Waterjet," Proceedings of the Winter Annual Meeting of ASME, 1989, pp. 37–42, which paper is incorporated herein by reference, first introduced and incorporated the concept of a "Machinability Number" into parameter prediction methods for determining optimum Abrasive Waterjet (AWJ) machining criteria (e.g., abrasive particle flow rate and traverse speed) to be used in order to achieve a desired surface quality for different materials to be machined.

Some AWJ systems manufacturers and their customers have attempted addressing the problem of determining the machinability numbers of materials by providing databases of machinability number data from trial-and-error, empirical tests performed by experienced AWJ operators on specific customer materials. This, however, involves considerable effort which is both costly and time-consuming. Such databases are also cumbersome and tedious to use.

The development of computer software has facilitated the use of databases of empirically obtained machinability number data to calculate the optimum operating criteria for materials for which the machinability number has been previously obtained. In the case a new material for which the machinability number is unknown is to be machined, the computer software may also be used to guide and assist an operator in conducting the empirical tests required to determine the machinability number from test pieces of the material.

The trial-and-error testing required to obtain machinability number data is wasteful, however, because it requires the use of numerous test pieces of material. Moreover, the testing is costly and time-consuming because it requires an AWJ machine operator to manually perform and evaluate the results of the testing, input the resultant empirical results, and program the machining parameters required for a subsequent machining operation to be performed.

The foregoing illustrates limitations known to exist in present machining methods and apparatus. Thus, it is apparent that it would be advantageous to provide an alternative directed to overcoming one or more of the limitations set forth above. Accordingly a suitable alternative is provided including features-more fully disclosed herein.

SUMMARY OF THE INVENTION

The present invention provides a method for measuring the machinability of a material which includes piercing a hole through a material to be tested while simultaneously measuring a pierce time duration, T, of the piercing step, and calculating a machinability number from the pierce time duration. Also provided are methods for determining the machining speed of a material and for machining a material which calculate a machining speed for a material based upon the machinability number of the material. The methods used to determine the machinability number and calculate a machining speed for a particular material can include a variety of machining operations including, but not limited to, AWJ milling processes.

Also provided is an apparatus which detects a pierce-through condition through a material made by a piercing force and the time duration the piercing force takes to create the pierce-through condition. The apparatus includes any of a pressure sensor, an acoustic sensor, an optical sensor, a load cell, a mechanical switch, and combinations thereof to measure the existence of a pierce-through condition. Apparatus including a controlling unit are also provided for obtaining predetermined stand-off and gap distances with a workpiece for a machining process. The controlling unit can further determine the thickness of a workpiece to be machined based upon the position of the nozzle assembly upon establishing the predetermined gap distance with the workpiece.

It is to be understood that both the foregoing general description and the following detailed description are exemplary, but are not restrictive, of the invention. The foregoing and other aspects will become apparent from the following detailed description when read in conjunction with the accompanying drawing figures.

DETAILED DESCRIPTION OF THE INVENTION

The apparatus and method of the present invention are best understood from the following detailed description when read in connection with the drawing figures in which like reference numerals refer to like elements throughout. It is emphasized that according to common practice, the various dimensions of the apparatus shown in the drawings are not to scale.

Figure 1:
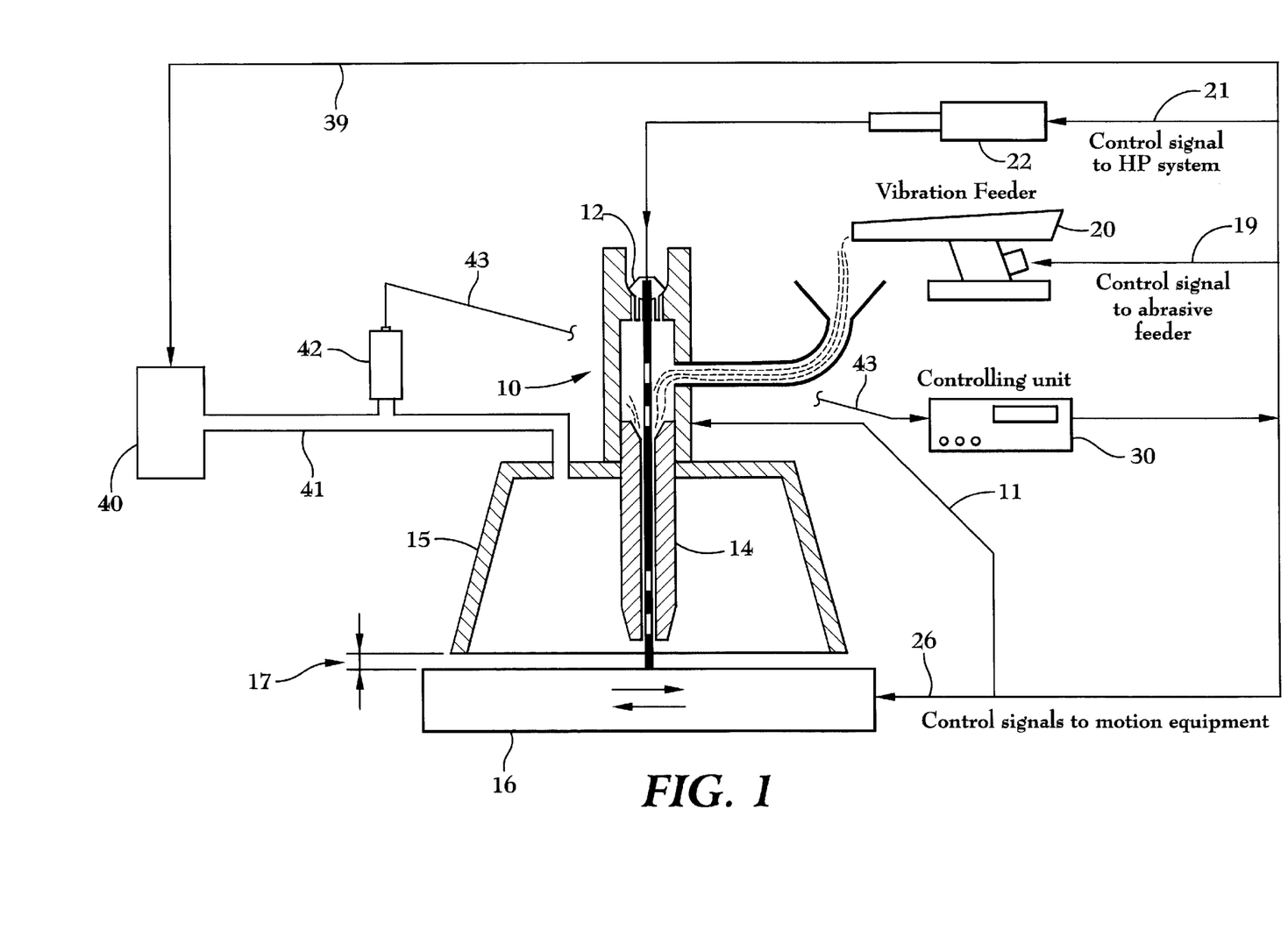
FIG. 1 is a general symbolic diagram of the components of an abrasive waterjet system according to the present invention.

Referring now to the drawing, FIG. 1 shows a broad system diagram of an embodiment of the invention as applied to an abrasive waterjet (AWJ) system. Abrasive water jet (AWJ) processes employ abrasive materials entrained into a high-pressure waterjet to perform a variety of milling and other machining operations on a variety of materials. The high-energy waterjet beam utilized combines a rapid erosion of a workpiece material by high speed solid particle impacts with rapid cooling provided by a waterjet. In AWJ milling operations, an abrasive waterjet removes material over a designated area at precisely controlled depths.

Briefly, shown in FIG. 1 is a nozzle assembly 10 comprised of an orifice 12 and a focusing tube 14 which applies a mixture of high pressure water and abrasive to a moving workpiece 16. Nozzle assembly 10 is preferably supplied abrasive from an optional vibration feeder 20 and high pressure water from a water source 22. Although shown using a vibration feeder, it is understood that other types of feeding devices, which are known and will be readily recognized by those having ordinary skill in the art, may be used for this purpose.

In performing AWJ processes, a number of parameters such as water pressure, abrasive particle size, abrasive flow rate, and the dimensions of the waterjet nozzle orifice are varied depending on the type of material to be milled. A controlling unit 30 is provided which controls the feed from vibration feeder 20 and the feed supply of high pressure water from water source 22. Prior to performing an AWJ milling operation, controlling unit 30 is typically preset by a user with the AWJ system operating parameters including "$d_o$", "$d_f$", "P", "A", and "D". The selection of these operating parameters for performing milling operations using an AWJ apparatus are described in detail below.

In operation, as high pressure water and abrasives are supplied to the nozzle, the workpiece 16 is moved back and forth by positioning equipment (not shown), as is known in the art, which maneuvers the workpiece for the desired milling operation responsive to a control signal provided by controlling unit 30. As described in detail below, controlling unit 30 receives input on the operating conditions of the AWJ system and calculates optimum milling speeds "$u_m$" for the material of workpiece 16 and accordingly controls the motion of workpiece 16 to provide the desired speed. Controlling unit 30 is preferably a Computerized Numerical Controller (CNC) which is available and known to those in the art and may include, e.g., the Model ACR 2000 motion controller which is available from Acroloop Motion Control Systems, Inc., Chanhassen, Minn.

AWJ Milling Equations and Operating Parameters

For a milling operation in which a waterjet moves across a workpiece to remove material to a depth "D" without piercing the thickness of a workpiece, the present inventor has discovered that the optimum traverse speed "$u_m$" may be estimated according to the following equation:

$$u_m = \left( \frac{N_{mm} \cdot P^{2.073} \cdot d_o^{0.897}}{4606 \cdot D} \right)^{1.17} \quad \text{[Eqn. 1]}$$

where "$d_o$" is the bore diameter (inches) of orifice 12; "P" is the water pressure (ksi) to be provided by high-pressure water source 22; and "D" is the depth (inches) of the material to be removed from the workpiece; and "$N_{mm}$" is the machinability number for milling the workpiece material.

The paper presented at the 9th American Waterjet Conference in Dearborn, Mich., on Aug. 23–26, 1997 by J. Zeng and J. Munoz titled "Milling Ceramics with Abrasive Waterjets—An Experimental Investigation" is incorporated herein by reference as providing typical process parameters for a milling operation. More specifically, typical operating parameters for performing an AWJ milling process using the apparatus described above are as follows:

Waterjet pressure (P): default set to 50 ksi, but varies depending on water pump capacity Orifice Bore Diameter ($d_o$): default set to 0.014 in, but varies depending on water pump capacity With respect to Eqn. 1 above, it is noted that this equation is empirically derived for an AWJ milling process and is conditioned on the use of specific values of the operating parameters $d_f$ (focusing tube bore diameter), A, and stand-off distance as follows:

Focusing Tube Bore Diameter ($d_f$): use tube having inner bore diameter approximately equal to $4.5 \cdot d_o$ Abrasive Flow Rate (A): set to $75 \cdot d_o$ lb/min (using Barton garnet #80)

Stand-Off Distance: set to $16 \cdot d_f$

Additionally, for milling operations requiring parallel passes to cover a desired milling area, Eqn. 1 is also conditioned upon using a lateral feed (i.e., side movement of nozzle between each parallel pass) set to $(\frac{2}{3}) \cdot d_f$.

The machinability number "$N_{mm}$" depends upon the type of the material upon which a milling operation is to be performed. Because the machinability number is a property of a specific material, it must be determined prior to performing a milling operation on a workpiece made of a type of material which has not been milled before. According to the present invention, the need for predetermining a machinability number for a material by multiple trial-and-error tests prior to performing a machining operation may be eliminated by the automatic machinability measuring and machining methods and the apparatus therefor provided herein.

The present inventor has discovered that the machinability number "$N_{mm}$" for a milling operation on a material is inversely related to the time "T" required by an AWJ waterjet to pierce through a material using a linear piercing motion having a thickness "h" according to the following empirical equation:

$$N_{mm} = \left( \frac{C_{tm} \cdot h^{1.571} \cdot d_o^{0.763}}{T \cdot P^{0.817} \cdot d_f^{0.806} \cdot A^{0.317}} \right) \quad \text{[Eqn. 2]}$$

where "$C_{tm}$" is a constant (which is 189,236 when calculating milling speed using dimensions for an inch-unit system) and "P" is the waterjet pressure (ksi); "$d_o$" is the bore diameter (inches) of orifice 12; "$d_f$" is the bore diameter (inches) of focusing tube 14; "A" is the abrasive flow rate (lbs/min) to be provided to nozzle assembly 10 by vibration feeder 20. Thus, by making a single test hole through a test coupon of material attached to a workpiece and incorporating a means for detecting the moment the waterjet pierces the workpiece, the machinability number for milling can be automatically calculated for the workpiece based upon the piercing time.

The thickness "h" is dictated by the size of the workpiece to be milled and is measured and inputted into controlling unit 30 either manually by a user or automatically using a thickness sensor according to the present invention as described in detail below.

Apparatus for Detecting Pierce-through of a Workpiece

In order to detect the moment a waterjet pierces a workpiece, a number of means may be incorporated. According to one embodiment of the present invention, as shown in FIG. 1 nozzle assembly 10 includes a nozzle shield 15 surrounding the focusing tube 14. Nozzle shield 15 is connected to and in fluid communication with an air or other gas supply 40 via a conduit 41. A pressure sensor 42 is connected to conduit 41 and located between nozzle shield 15 and air supply 40 for sensing the pressure conditions inside nozzle shield 15 and providing a pressure sensor signal 43 to controlling unit 30.

Operation for Performing Automated AWJ Milling

Figure 4A:
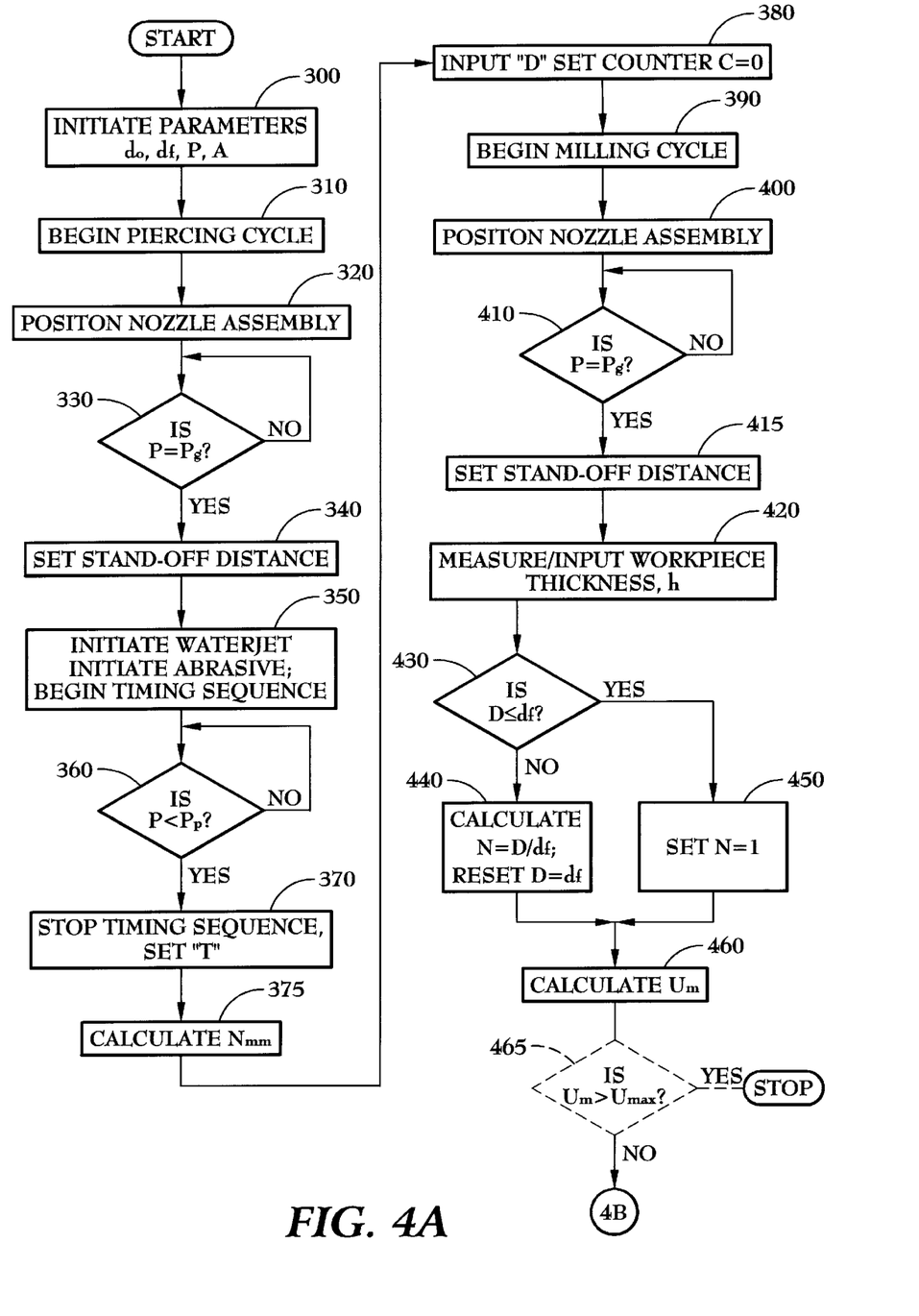
FIGS. 4A and 4B are program flow charts for a software program resident in the programmable controlling unit of FIG. 1 for performing a milling method according to an embodiment of the present invention.
Figure 4B:
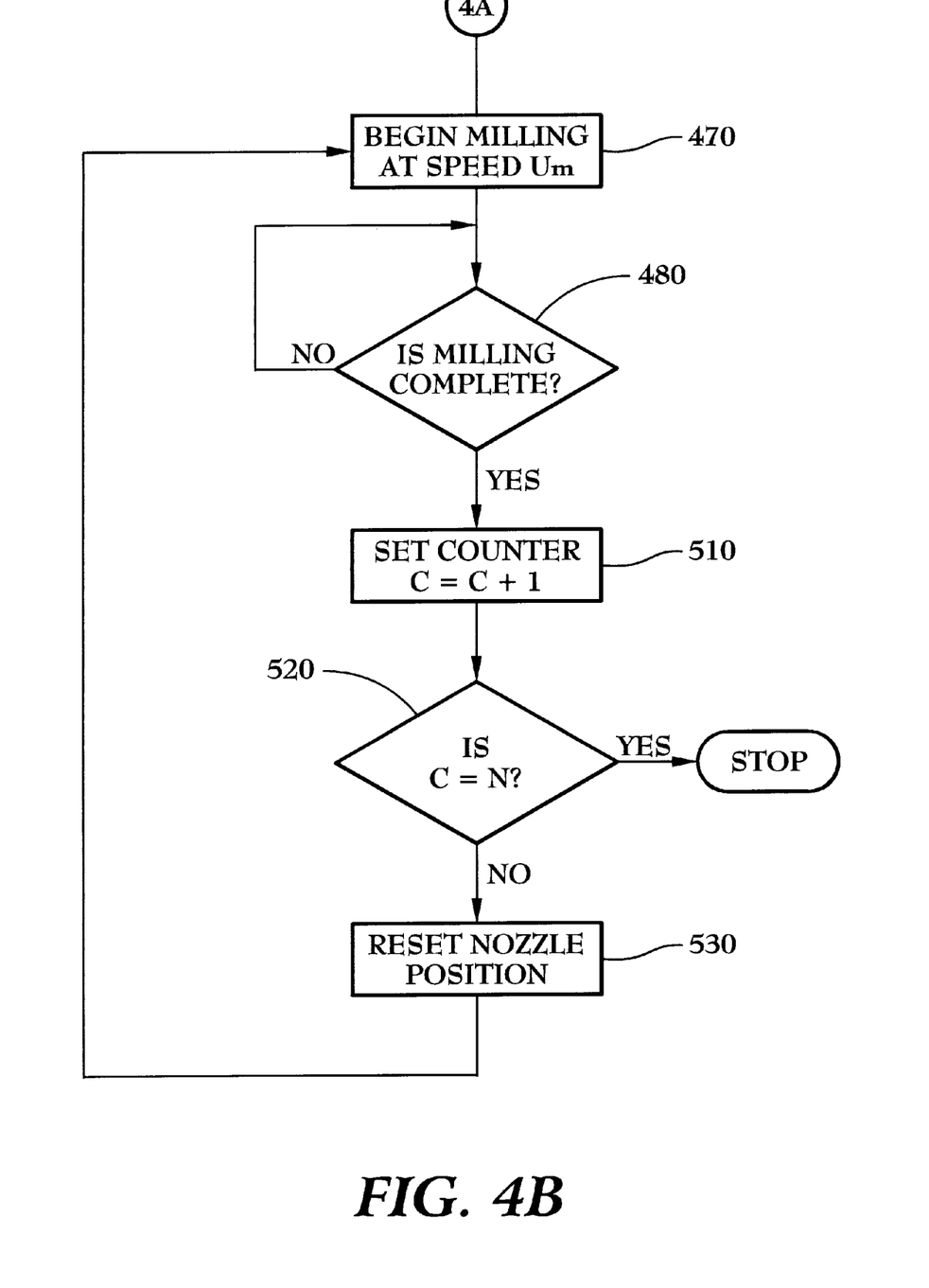

Operation of the AWJ apparatus shown in FIG. 1 will be described with respect to performing an AWJ milling operation according to the present invention. Turning to the flow diagram in FIGS. 4A and 4B, controlling unit 30 is initialized in Step 300 by inputting the specific AWJ system operating parameters including "$d_o$", "$d_f$", "P", and "A".

Because a waterjet milling operation only removes a portion of the material of a workpiece and does not penetrate the thickness of the workpiece material, if the machinability number $N_{mm}$ for milling the workpiece material is unknown, a piercing test is first performed on a testpiece made of the same material as the workpiece.

A. Positioning Nozzle Assembly at a Predetermined Stand-Off Distance

Controlling unit 30, upon receiving a user instruction to begin a milling sequence, begins a piercing cycle in Step 310 by generating a control signal 39 in Step 310 to air supply 40 thereby initiating airflow into nozzle shield 15 via conduit 41. Controlling unit 30 generates a control signal 11 instructing motion equipment (not shown) to lower nozzle assembly in Step 320 to form an air gap 17 having a pre-determined height which is approximately equal to the stand-off distance (i.e., the distance between the focusing tube 14 and workpiece 16).

Figure 2:
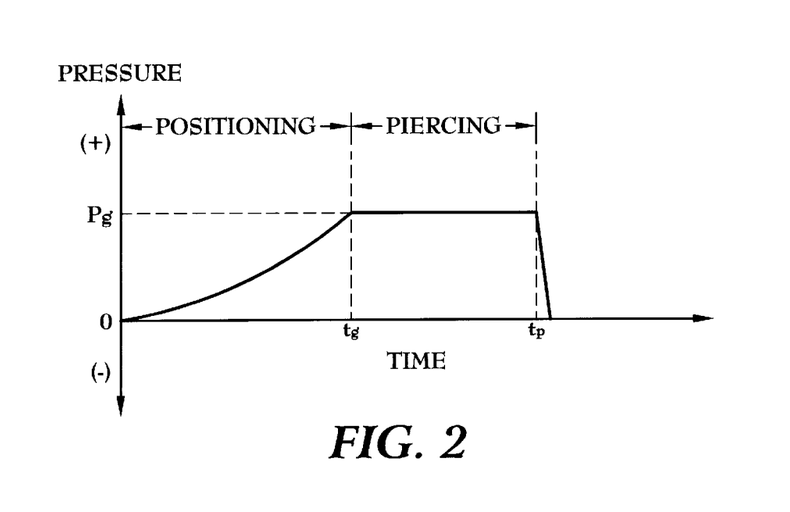
FIG. 2 is a representation of the pressure signal read by a pressure sensor during a piercing operation performed as part of the milling method according to one embodiment of the present invention.

This is accomplished by using pressure sensor 42 as a proximity switch which monitors in Step 330 the pressure increase caused by the restriction created between workpiece 16 and nozzle shield 15 as it moves toward the target surface. Thus, the stand-off and air gap distances are established by first establishing a known-air gap distance which, as shown in FIG. 2, corresponds to a predetermined pressure, $P_g$, which value is programmed into controlling unit 30. When in Step 330 it is detected that the pressure inside nozzle shield 15 has reached the predetermined pressure $P_g$, controlling unit 30 generates a control signal to stop the motion of the nozzle assembly 10 in Step 340 to set the desired stand-off distance.

B. Piercing the Workpiece and Calculating Machinability Number

In Step 350, controlling unit 30 simultaneously generates control signals 21 and 19 to, respectively, initiate the supply of high pressure water from water source 22 and abrasive from vibration feeder 20 to establish an abrasive water jet in water nozzle assembly 10. Controlling unit 30 also begins a timing sequence and until workpiece 16 is pierced. During the time the piercing operation is being performed, air supply 40 continues to provide a steady flow of air to nozzle shield 15 while pressure sensor 42 monitors and provides a steady output signal 43 to controlling unit 30 as represented by the horizontal signal between "$t_g$" and "$t_p$". Upon penetration (i.e., "pierce-through") of the waterjet through workpiece 16, a vacuum is created within nozzle shield 15 which, as shown in FIG. 2, causes a virtually instantaneous drop in the pressure detected by pressure sensor 42 at "$t_p$", which is the moment pierce-through occurs.

Upon detecting the decrease in pressure in Step 360 caused upon pierce-through, controlling unit 30 stops the timing sequence in Step 370 and obtains and records the pierce-through time "T". In Step 375, controlling unit 30 calculates and stores the machinability number "$N_{mm}$" for milling according to Eqn. 2 set forth above which is programmed into controlling unit 30.

C. Milling the Workpiece

The workpiece 16 to be milled is then placed under nozzle assembly 10. The desired depth "D" of the material to be removed from the workpiece is programmed into controlling unit 30 and a counter is set to zero in Step 380 for tracking the number of milling passes made by the nozzle assembly 10. Upon receiving a user instruction in Step 390 to begin a milling sequence, controlling unit 30 generates a control signal 11 instructing motion equipment (not shown) to position nozzle assembly 10 in Steps 400, 410, and 415 to establish stand-off and air gap distances over workpiece 16 in the same manner as described in Steps 320, 330, and 340, respectively, for the piercing operation above. Because the typical stand-off distance used for AWJ milling operations are relatively large (typically set at approximately one inch), when in Step 410 it is detected that the pressure inside nozzle shield 15 has reached the predetermined pressure $P_g$, controlling unit 30 generates a control signal to reverse the motion of the nozzle assembly 10 in Step 340 to set the desired stand-off distance.

D. Determining Workpiece Thickness

The thickness "h" of workpiece 16 may be automatically measured and inputted into controlling unit 30. This is accomplished in Step 420 by comparing the height of nozzle assembly in the cutting position with a known reference position and calculating the thickness of the workpiece. Alternatively, the thickness "h" may be measured manually by the operator and inputted into controlling unit 30 in Step 420.

In Step 430, controlling unit 30 first compares the bore diameter (inches) of focusing tube 14, "$d_f$", against the desired milling depth, "D." If the desired milling depth "D" is larger than "$d_f$", then the milling operation is then performed in an integer number, "N", of overlapped milling passes determined in Step 440 according to the following equation:

$$N = D/d_f \quad \text{[Eqn. 3]}$$

The value of "D" is then reset to equal the bore diameter of focusing tube 14, "$d_f$" in step 440 and the traverse speed "$u_m$" for the overlapped milling passes is calculated in Step 460 according to Eqn. 1 set forth above.

If, however, in Step 430 the desired depth "D" is smaller than or equal to "$d_f$", then in Step 450, "N" is set to equal one and the desired depth "D" is used in Step 460 along with the stored machinability number "$N_{mm}$" to calculate the traverse speed "$u_m$" according to Eqn. 1 set forth above.

Additionally, in an optional step 465, controlling unit 30 may be programmed to check the calculated traverse speed "$u_m$" required against a maximum speed "$U_{max}$" which is the limit of the AWJ apparatus limit of speed. If $u_m > u_{max}$, then controlling unit 30 prevents the milling operation and generates an error message that the operation is not feasible.

The desired milling operation is then initiated in Step 470 by controlling unit 30 which simultaneously generates control signals 21 and 19 to, respectively, initiate the supply of high pressure water from water source 22 and abrasive from vibration feeder 20 to establish an abrasive water jet in water nozzle assembly 10. Controlling unit 30 also sends a control signal 11 to begin the movement of nozzle assembly 10 and/or a control signal 26 to begin the movement of workpiece 16 at the calculated milling speed "$U_m$". Preferably, a mask is cut based on the CAD file of the workpiece part and used to protect and to achieve a better edge quality in the surrounding workpiece material which is not to be milled.

The milling process may comprise parallel passes to cover a desired milling area. Preferably, controlling unit 30 is programmed to perform both multiple parallel passes and multiple layers of passes to cover the desired milling area and depth of milling.

When controlling unit detects in Step 480 that one layer of the milling operation is complete, the counter in step 510 is increased by one and then compared in step 520 to determine whether the desired set number of milling layers "N" has been performed. If not, then the milling operation repeats by controlling unit 30 resetting the nozzle position by moving nozzle assembly 10 and/or workpiece 16 in step 530 and returning to begin another milling layer in Step 470. The milling process is continued until the desired number of milling layers, "N", have been performed and detected in Step 520 at which point the milling operation is ended.

As discussed above the milling operation is described as including a preliminary piercing test on a testpiece which is separated from a workpiece 16 to be subsequently milled, thus requiring the testpiece to be replaced by the workpiece between steps 375 and 380. Alternatively, to provide for a "drop-and-mill" operation, a test coupon may be provided on the workpiece so that the milling operation may be performed immediately following the piercing operation. The test coupon may then be cut off after the AWJ milling operation is complete.

Pressure Sensors and Alternative Pierce-through Detection Devices

With respect to devices which may be incorporated as pressure sensor 42, any sensor which can detect the decrease of pressure which occurs within nozzle shield 15 upon pierce through may be incorporated. An exemplary device includes, but is not limited to, a Model OKC-424 Air Proximity Sensor, available form O'Keefe Controls Co., Monroe, Conn.

Figure 5:
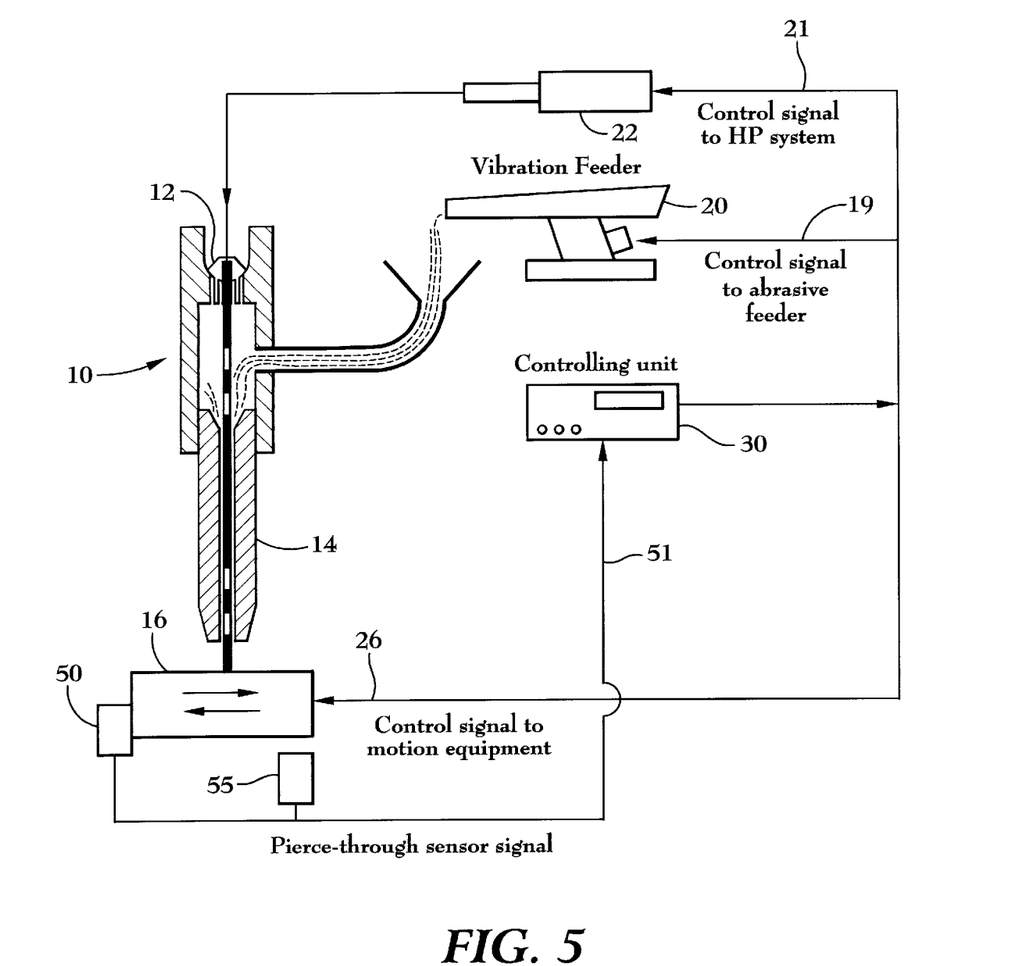
FIGS. 5 and 6 are general symbolic diagrams showing alternative embodiments of pierce-through detection devices according to the present invention.

Although described above with respect to the use of pressure sensor 42 and air supply 40 for detecting pierce time, it will be readily understood based on and upon reading the teachings of this disclosure, that other sensors may be incorporated to detect the moment of pierce-through by a waterjet. Shown in FIG. 5 are alternative pierce-through detectors 50 and 55 which, respectively, may be attached to or used in the vicinity of a workpiece 16 upon which an AWJ operation is being performed. Pierce-through detectors 50 and 55 may be used individually or in combination. Exemplary detectors which may be used in this fashion include, but are not limited to conventional sensors, which can either directly detect the presence of the waterjet upon piercethrough (e.g., by means of an optical sensor) or indirectly detect some characteristic change which occurs upon pierce through (e.g., by means of an acoustic sensor or a load cell).

Figure 3:
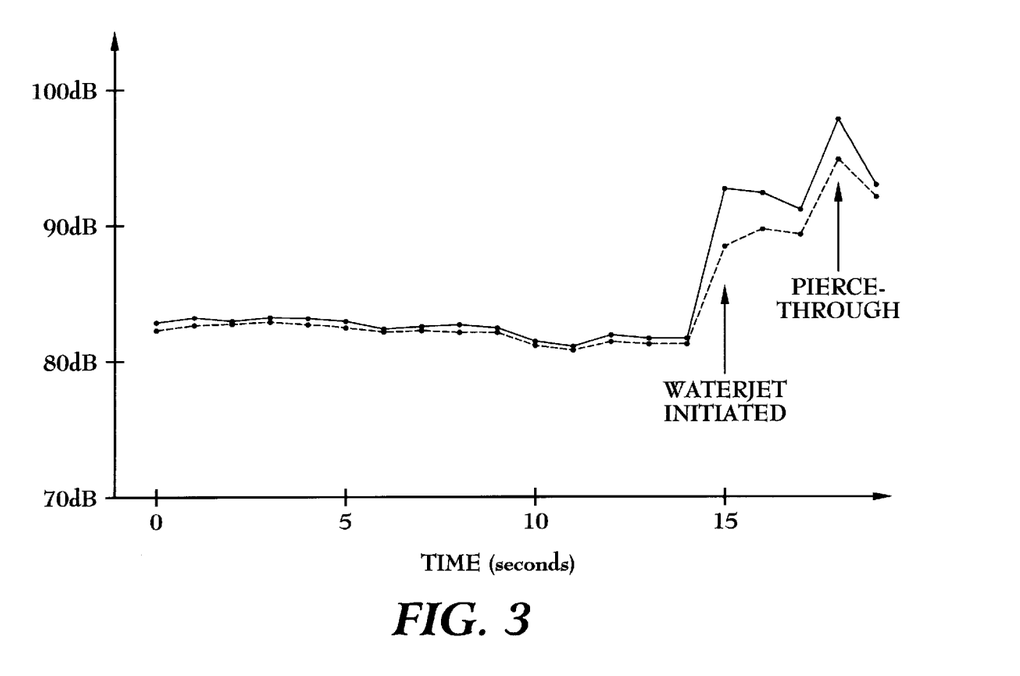
FIG. 3 shows a reproduction of the wave form actually generated by an acoustic sensor used in one embodiment of the present invention.

Acoustic sensors useful in this regard are those which can detect the change in sound level which occurs upon pierce through and include an acoustic sensor such as the Model 2800 Integrating Sound Level Meter available from Quest Technologies, Inc., Oconomowoc, Wis. Shown in FIG. 3 is a reproduction of the acoustic readings obtained during an AWJ piercing operation using an acoustic sensor with the initiation of the waterjet operation and the moment of pierce-through clearly indicated by two separate and distinct peaks. Load cells also useful in this regard are those which can detect the decrease in the force exerted on workpiece 16 by a waterjet which occurs upon pierce-through and may include load cells such as those available from Sens-All, Inc., Southington, Conn.

Figure 6:
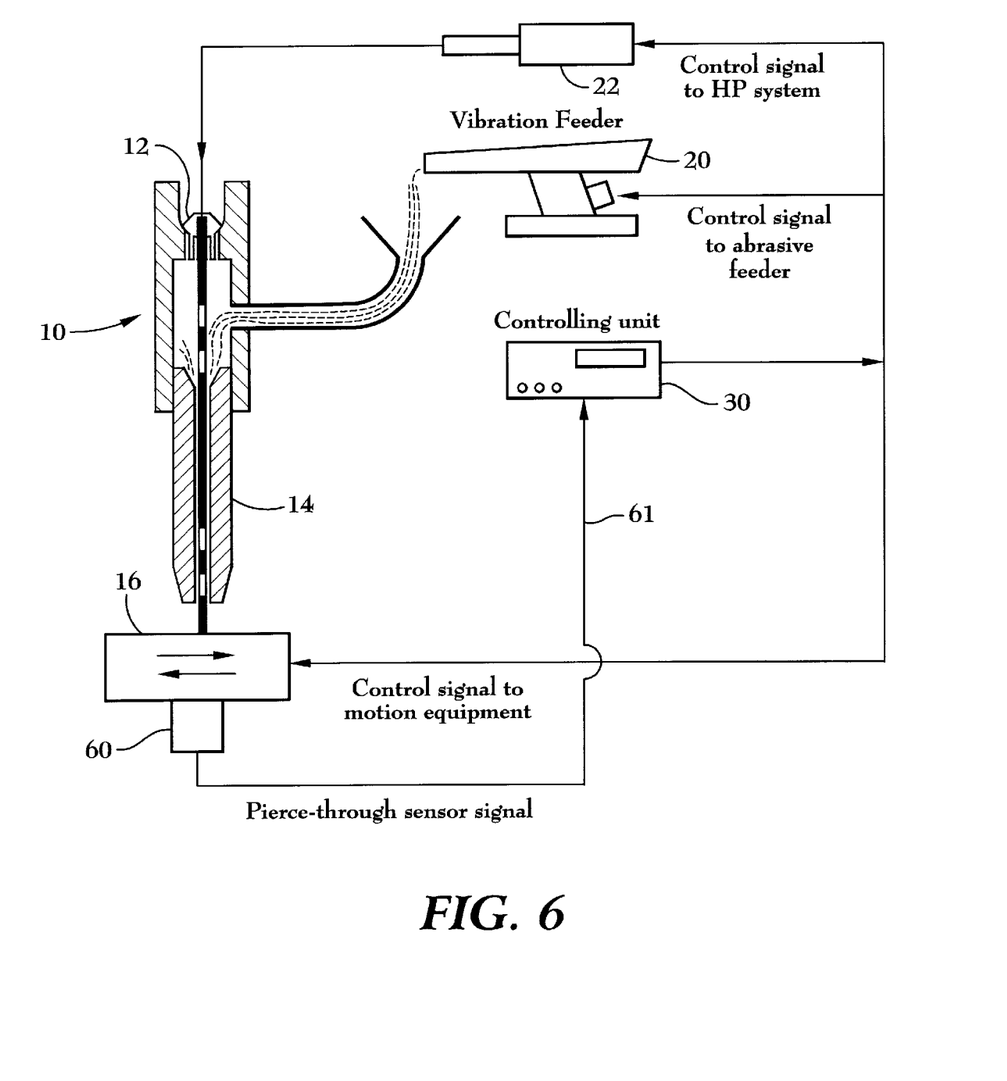

Alternatively, as shown in FIG. 6 a conventional mechanical switch 60, as is known in the art, may be located directly under workpiece 16 such that upon penetration by the waterjet, the switch 60 is tripped thereby indicating to controlling unit 30 the existence of a pierce-through condition.

As a result of the apparatus and method of the present invention, an AWJ system is provided which provides a number of advantages over prior art milling and other machining processes. Among these advantages is the ability to determine using the automated machining processes according to the present invention which determine the optimum machining parameters for an AWJ operation without the need for multiple trial-and-error testing or extensive user experience for machining new materials. Moreover, according to the present invention, a continuous milling process may be provided by incorporating a test coupon on the workpiece. By sequentially piercing a test hole in the test coupon and proceeding without interruption to a milling operation, a continuous milling operation may be achieved. The test piece is later removed by cutting.

Moreover, automatic programming of the machining speeds during operation may be accomplished without the need for any user interference or interface while also increasing the accuracy of the optimum machining speeds so determined. Furthermore, various control and measurement functions may be automatically accomplished using the apparatus and method of the present invention including, proximity detection of a workpiece with respect to a waterjet nozzle and measuring the thickness of a workpiece. Additionally, compensation for changes in process parameters (e.g., changes in water pressure, abrasive flow rate, abrasive type, nozzle diameter, etc.) may also be made automatically.

Alternative Embodiments to Additional Machining Technologies

Although illustrated and described herein with reference to certain specific embodiments, namely, AWJ milling energy beam machining processes, the present invention is nevertheless not intended to be limited to the details shown. Rather, various modifications may be made in the details in the scope and range of equivalents of the claims without departing from the spirit of the invention. Such modifications may include the application of the apparatus and method for determining the machinability numbers using other energy beam machining technologies in addition to AWJ milling processes. Moreover, it is envisioned that the determination of machinability numbers of engineering material according to the present invention using one energy beam process may be applied to or otherwise correlated with calculating process parameters for use in other types of energy beam machining processes.

Such energy beam technologies include those which utilize a concentrated beam energy to effect material removal to cut or otherwise make, shape, prepare, or finish (i.e., machine) a raw stock material into a finished material. By way of example, it is envisioned that the apparatus and method of the present invention may be adapted for incorporation into other types of energy beam technologies, including but not limited to, pure waterjet, laser, plasma arc, flame cutting, and electron beam technologies. Although each of these use different physical phenomena to remove material, they behave similarly in nature and methodology to a waterjet energy beam such that the apparatus and method of the present invention may be employed.

Furthermore, it is to be understood that the selection of other energy beam technologies to which the present invention may be applied is not limited to these specific examples which are merely illustrative. Rather, these energy beam technologies will be readily recognized and may be selected by those having ordinary skill in the art upon analyzing the following features and as taught by the present inventor and set forth below relative to an AWJ process:

Energy Delivery Relationships:

AWJ: The higher the applied flow/pressure (hp/watts), the faster the material removal rate.

Laser: The higher the applied output power (hp/watts), the faster the material removal rate.

Plasma: The higher the applied flow/pressure (hp/watts), the faster the material removal rate.

Analytical Relationships:

AWJ: Machining (e.g., milling, turning) removal rates can be related to a machinability number.

Laser: Machining removal rates can be related to a machinability number.

Thus, it is envisioned that the method and apparatus of the present invention may be used to determine the machinability number for other energy beam processes (e.g., laser and plasma energy beam processes) which cause material responses similar to those set forth above for a waterjet process. Additionally, it is further envisioned that the energy beam processes including AWJ may be used to perform a variety of other AWJ and traditional operations such as piercing, drilling, and turning operations.

What is claimed is:

1. A method for measuring the machinability of a material, comprising the steps of:
   a) providing a material;
   b) piercing said material;
   c) simultaneously measuring a pierce time duration, T, of said piercing step; and
   d) calculating a machinability number from said pierce time duration, said machinability number being other than a piercing machinability number.

2. A method for measuring the machinability of a material according to claim 1 wherein said piercing step is performed using a concentrated beam energy.

3. A method for measuring the machinability of a material according to claim 2 wherein said concentrated beam energy is a beam energy selected from the group consisting of an abrasive waterjet, a pure waterjet, a laser, a plasma arc, a flame, and an electron beam.

4. A method for measuring the machinability of a material according to claim 1 wherein said piercing step is performed by an abrasive waterjet process.

5. A method for measuring the machinability of a material according to claim 4 wherein said step of calculating a machinability number is according to the following equation to obtain the machinability number, $N_{mm}$, for a milling process:

$$N_{mm} = \left( \frac{C_{tm} \cdot h^{1.571} \cdot d_o^{0.763}}{T \cdot P^{0.817} \cdot d_f^{0.806} \cdot A^{0.317}} \right).$$

6. A method for measuring the machinability of a material according to claim 5 wherein said milling process is an abrasive waterjet milling process.

7. A method for determining the machining speed of a material, comprising the steps of:
   a) providing a material;
   b) piercing said material;
   c) simultaneously measuring a pierce time duration, T, of said piercing step;
   d) calculating a machinability number from said pierce time duration, said machinability number being other than a piercing machinability number; and
   e) calculating a speed at which said material is to be machined from said machinability number.

8. A method for determining the machining speed of a material according to claim 7 wherein said piercing step is performed using a concentrated beam energy.

9. A method for determining the machining speed of a material according to claim 8 wherein said concentrated beam energy is a beam energy selected from the group consisting of an abrasive waterjet, a pure waterjet, a laser, a plasma arc, a flame, and an electron beam.

10. A method for determining the machining speed of a material according to claim 7 wherein said piercing step is performed by an abrasive waterjet process.

11. A method for determining the machining speed of a material according to claim 10 wherein said step of calculating a machinability number is performed to obtain the machinability number, $N_{mm}$, for a milling process according to the following equation:

$$N_{mm} = \left( \frac{C_{tm} \cdot h^{1.571} \cdot d_o^{0.763}}{T \cdot P^{0.817} \cdot d_f^{0.806} \cdot A^{0.317}} \right).$$

12. A method for determining the machining speed of a material according to claim 11 wherein said step of calculating a speed at which said material is to be machined is according to the following equation to obtain a milling speed, $u_m$, for an abrasive waterjet milling process:

$$u_m = \left( \frac{N_{mm} \cdot P^{2.073} \cdot d_o^{0.897}}{4606 \cdot D} \right)^{1.17}.$$

13. A method for machining a material, comprising the steps of:
   a) providing a sample comprising a material to be machined;
   b) piercing a hole through said sample;
   c) simultaneously measuring a pierce time duration, T, of said piercing step;
   d) calculating a machinability number for said material from said pierce time duration, said machinability number being other than a piercing machinability number;
   e) calculating a speed at which a workpiece comprising said material is to be machined from said machinability number; and
   f) machining a workpiece comprising said material at said calculated speed.

14. A method of machining a material according to claim 13 wherein said piercing step is performed using a concentrated beam energy.

15. A method of machining a material according to claim 14 wherein said concentrated beam energy is a beam energy selected from the group consisting of an abrasive waterjet, a pure waterjet, a laser, a plasma arc, a flame, and an electron beam.

16. A method of machining a material according to claim 13 wherein said step of machining is performed using a concentrated beam energy.

17. A method of machining a material according to claim 16 wherein said concentrated beam energy is a beam energy selected from the group consisting of an abrasive waterjet, a pure waterjet, a laser, a plasma arc, a flame, and an electron beam.

18. A method of machining a material according to claim 13 wherein said step of machining is a machining operation selected from the group consisting of a piercing, a drilling, and a turning operation, and combinations thereof.

19. A method for machining a material according to claim 13 wherein said piercing step is performed by an abrasive waterjet process.

20. A method for machining a material according to claim 19 wherein said step of machining comprises a milling process; and said step of calculating a machinability number is according to the following equation to obtain the machinability number, $N_{mm}$, for said milling process:

$$N_{mm} = \left( \frac{C_{tm} \cdot h^{1.571} \cdot d_o^{0.763}}{T \cdot P^{0.817} \cdot d_f^{0.806} \cdot A^{0.317}} \right).$$

21. A method for machining a material according to claim 20 wherein said step of machining comprises an abrasive waterjet milling process; and said step of calculating a speed at which said workpiece is to be machined is according to the following equation to obtain a milling speed, $u_m$, for said abrasive waterjet milling process:

$$u_m = \left( \frac{N_{mm} \cdot P^{2.073} \cdot d_o^{0.897}}{4606 \cdot D} \right)^{1.17}.$$

22. A method for machining a material according to claim 13 wherein said workpiece which is machined in said machining step comprises said sample which is pierced in said piercing step.

* * * * *